(12) United States Patent
Rasche

(10) Patent No.: US 7,603,159 B2
(45) Date of Patent: Oct. 13, 2009

(54) METHOD FOR TRANSCUTANEOUS CATHETER GUIDING

(75) Inventor: Volker Rasche, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 796 days.

(21) Appl. No.: 10/513,011

(22) PCT Filed: Apr. 29, 2003

(86) PCT No.: PCT/IB03/01649

§ 371 (c)(1), (2), (4) Date: Oct. 28, 2004

(87) PCT Pub. No.: WO03/092488

PCT Pub. Date: Nov. 13, 2003

(65) Prior Publication Data

US 2005/0171426 A1 Aug. 4, 2005

(30) Foreign Application Priority Data

May 2, 2002 (DE) .............................. 102 19 594

(51) Int. Cl.
*A61B 5/05* (2006.01)

(52) U.S. Cl. .................. 600/424; 600/459; 600/462; 600/585; 604/510

(58) Field of Classification Search .............. 600/424, 600/434–435, 462–464; 604/95.01, 510
See application file for complete search history.

(56) References Cited

U.S. PATENT DOCUMENTS

| | | | | |
|---|---|---|---|---|
| 4,431,005 A | * | 2/1984 | McCormick | 600/433 |
| 5,095,911 A | * | 3/1992 | Pomeranz | 600/463 |
| 5,289,373 A | * | 2/1994 | Zarge et al. | 600/434 |
| 5,421,338 A | * | 6/1995 | Crowley et al. | 600/463 |
| 5,577,502 A | * | 11/1996 | Darrow et al. | 600/426 |
| 5,779,623 A | * | 7/1998 | Bonnell | 600/114 |
| 5,779,643 A | * | 7/1998 | Lum et al. | 600/462 |
| 5,938,609 A | * | 8/1999 | Pomeranz | 600/439 |
| 6,016,439 A | * | 1/2000 | Acker | 600/411 |
| 6,050,958 A | * | 4/2000 | Dickinson et al. | 600/585 |
| 6,078,831 A | * | 6/2000 | Belef et al. | 600/424 |
| 6,226,543 B1 | * | 5/2001 | Gilboa et al. | 600/407 |
| 6,246,898 B1 | * | 6/2001 | Vesely et al. | 600/424 |
| 6,275,724 B1 | * | 8/2001 | Dickinson et al. | 600/424 |
| 6,332,089 B1 | * | 12/2001 | Acker et al. | 600/424 |
| 6,371,928 B1 | * | 4/2002 | Mcfann et al. | 600/585 |
| 6,406,442 B1 | * | 6/2002 | McFann et al. | 600/585 |
| 6,493,575 B1 | * | 12/2002 | Kesten et al. | 600/431 |
| 6,612,992 B1 | * | 9/2003 | Hossack et al. | 600/467 |

(Continued)

*Primary Examiner*—Long V Le
*Assistant Examiner*—Salieu M Abraham

(57) ABSTRACT

The invention relates to a method of determining the position of a catheter introduced along a guide wire inserted into a body, in which method an image of the guide wire and the body region at the area of the guide wire is acquired by means of an imaging method, the distance traveled by the catheter on the guide wire is measured and the position of the catheter in the body is determined on the basis of the measured distance. The invention also relates to a device for determining the position of a catheter introduced along a guide wire inserted into a body, which device includes sensor means for measuring the distance traveled by the catheter on the guide wire and means for determining the position of the catheter on the basis of the measured distance.

13 Claims, 2 Drawing Sheets

FIG.2

U.S. PATENT DOCUMENTS

Figure 1:
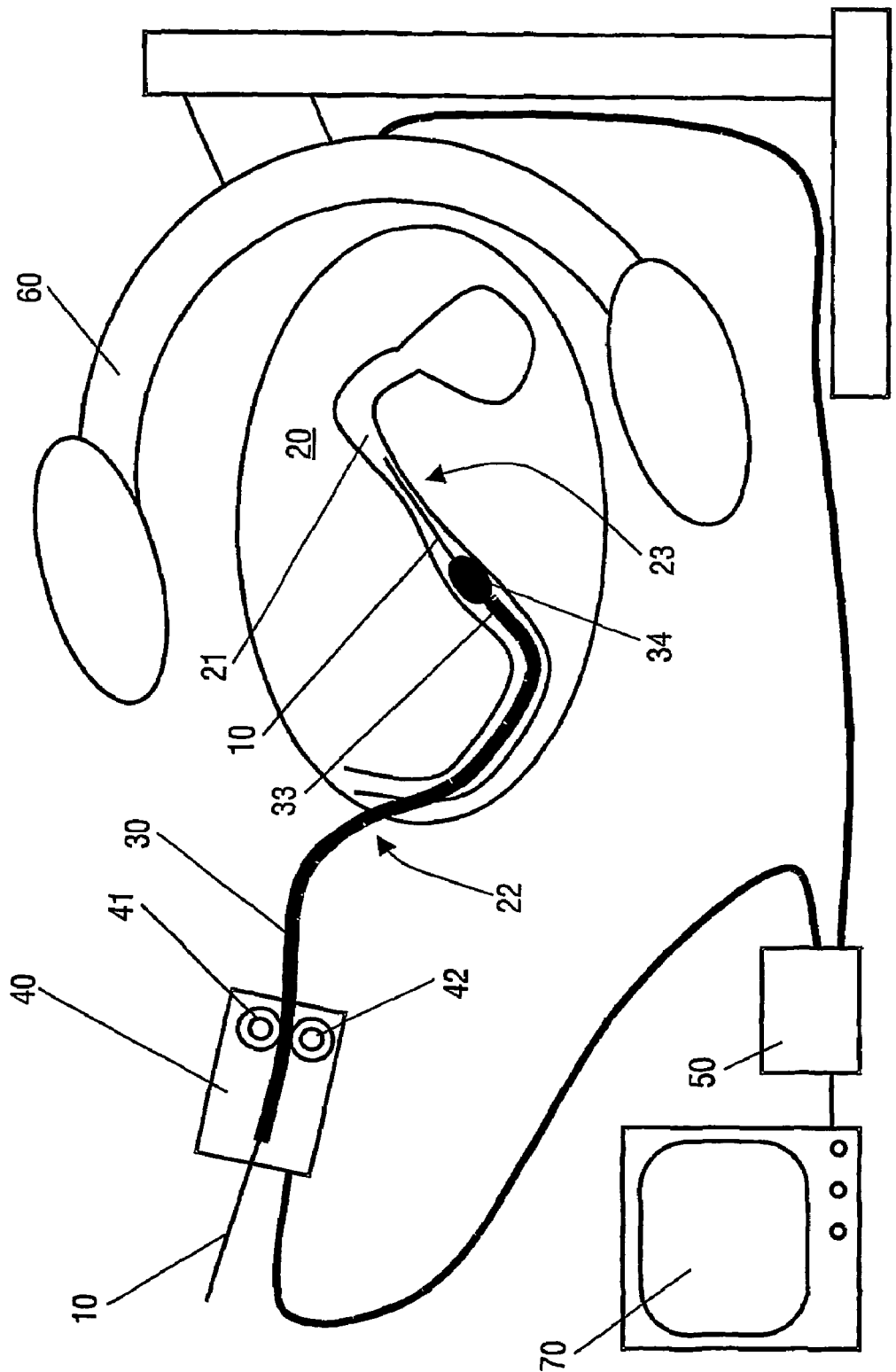

| | | | |
|---|---|---|---|
| 6,711,429 B1 * | 3/2004 | Gilboa et al. | 600/407 |
| 6,895,267 B2 * | 5/2005 | Panescu et al. | 600/424 |
| 7,066,924 B1 * | 6/2006 | Garibaldi et al. | 604/510 |
| 7,276,044 B2 * | 10/2007 | Ferry et al. | 604/95.01 |
| 2001/0029337 A1 * | 10/2001 | Pantages et al. | 600/463 |
| 2001/0031919 A1 * | 10/2001 | Strommer et al. | 600/424 |
| 2003/0073900 A1 * | 4/2003 | Senarith et al. | 600/424 |
| 2006/0041245 A1 * | 2/2006 | Ferry et al. | 604/510 |

* cited by examiner

METHOD FOR TRANSCUTANEOUS CATHETER GUIDING

The invention relates to a method of determining the position of a catheter introduced along a guide wire inserted into a body, in which method an image of the guide wire and the body region at the area of the guide wire is acquired by means of an imaging method.

In order to determine the position of the catheter in known methods of the kind set forth, an imaging method is regularly carried out in order to acquire images of the relevant body regions with the inserted guide wire and the catheter introduced along this guide wire, thus enabling determination of the position of the catheter. Depending on the requirements imposed as regards the accuracy of the positioning of the catheter, or the tip of the catheter, several image acquisition procedures have to be carried out so as to enable repeated checking of the position of the catheter. Such repeated image acquisition is a costly procedure. Furthermore, notably when an X-ray imaging method (fluoroscopy) is used, the repeated image acquisitions lead to a substantial radiation load for the patient as well as for the medical staff.

It is an object of the invention to provide a method which enables a simplified determination of the catheter position and reduces the radiation load.

The object is achieved in accordance with the invention by measuring the distance traveled by the catheter on the guide wire and by determining the position of the catheter in the body on the basis of the measured distance.

Because the catheter is fed forwards on the guide wire, the catheter or the catheter tip can only be situated along the guide wire. When the position of the guide wire relative to the lesion is known, therefore, the position of the catheter can be determined as a function of the distance traveled by the catheter or the tip of the catheter on the guide wire. As a result, after the position of the guide wire in relation to the lesion in the body and the body region around the guide wire have been determined once, the position of the catheter or the tip of the catheter in the body region can be determined at any instant by measuring how far the catheter has traveled on the guide wire. The determination of the position of the catheter thus requires only a single acquisition of an image of the body region and the guide wire, so that the radiation load caused by the repeated image acquisitions can be avoided.

Furthermore, the position of the catheter or the catheter tip can be determined permanently and in real time, whereas according to the known method the position of the catheter or the catheter tip can be determined only at given instants, that is, the instants of image acquisition. The method in accordance with the invention thus enables a reduction of the radiation load, a simplified determination of the position of the catheter/the tip of the catheter, and a permanent and real-time determination and display of the position of the catheter.

In accordance with a first advantageous version of the method in accordance with the invention an image of the body region is acquired and the position of the catheter is displayed in this image. This image can be acquired before, during or after the determination of the position of the catheter.

The body region, and possibly the guide wire introduced into this body region, can then be determined from the image data previously acquired by means of the imaging method, the position of the catheter can be determined, as described before, on the basis of the measured distance and be displayed in the image of the body region. In this preferred version imaging can take place at regular intervals, for example, at instants specified by the user, or a plurality of images can be formed in rapid succession, thus enabling permanent real-time observation of the catheter/the tip of the catheter and hence of the progress of the catheter.

In accordance with a further advantageous version the imaging of the body region and the guide wire is realized by means of a two-dimensional or three-dimensional imaging method. All types of medical imaging methods can be used for this purpose. Use can advantageously be made of X-ray imaging methods, that is, two-dimensional X-ray projections or computed tomography X-ray imaging methods. For the visualization of vascular systems, a contrast medium can then be advantageously administered so as to be imaged by the imaging method. Customary methods in this respect are angiography methods, in particular fluoroscopic angiography.

For the above version of the method in accordance with the invention the body region and the guide wire can be advantageously imaged by way of two essentially orthogonal projections, a three-dimensional image of the body region being formed from such projections by way of modeling. Modeling is performed by means of numerical calculation from the image data acquired by way of the projections. The modeling notably enables the formation of a coronary roadmap. Customary methods can be used for the modeling operation. The projections can be acquired either simultaneously by means of a two-plane system or successively by means of a mono-plane system. In the case of temporally successive projections it is advantageous to acquire the projections in the same cardiac phase when the method in accordance with the invention is used for the imaging of the vascular system, notably in the region of the heart.

It can be advantageously arranged in particular that the acquisition of the image data is realized by means of images of the body regions which have been shifted in time and triggered on the basis of the cardiac frequency. The successively acquired image data can be compared and possibly superposed in this manner. Furthermore, if the image data from images of the same cardiac phase is available, a three-dimensional image can be modeled from such image data without it being necessary to carry out any complex reconstruction methods, distortion correction methods and/or image data allocation operations.

In a further advantageous version of the method in accordance with the invention an image of the body region with the guide wire and the inserted catheter is acquired and displayed after the determination of the position of the catheter. This postponed acquisition of image data serves to compare the calculated (virtual) image data on the position of the catheter with the actual position of the catheter. This approach serves to check the calculated catheter position. It can then be arranged, for example, to perform an image data acquisition at given time intervals and to compare the catheter position visualized from this image acquisition with the numerically calculated catheter position at the relevant instant and to perform, if necessary, a correction of the calculation data. It may also be arranged to couple the image acquisition means to the sensor means so as to carry out an image data acquisition operation for given traveled distances, notably when the target position or a region around the target position is reached.

The invention also relates to a device for determining the position of a catheter introduced along a guide wire inserted into a body, which device includes sensor means for measuring the distance traveled by the catheter on the guide wire and means for determining the position of the catheter on the basis of the measured distance.

In a very simple embodiment of the invention it is possible to predetermine merely a desired position of the catheter and to calculate the distance of travel of the catheter on the guide wire which is necessary for this position of the catheter. Subsequently, the catheter is displaced on the guide wire until the desired distance has been traveled, said distance being determined by means of simple measuring means such as, for example, a centimeter tape, a caliper gage or the like.

Furthermore, sensors which are known for the purpose of length sensing, for example, inductive or potentiometric distance sensors, can be used to determine the distance. Such distance sensors may be coupled to display or signal means which indicate the relevant distance of travel and/or trigger a signal, for example, an optical or acoustic signal, when a given reference distance is reached.

The device in accordance with the invention may also include image acquisition means which are arranged to acquire an image of the inserted guide wire and the body region of the guide wire. Such image acquisition means can also be constructed so as to co-operate with the sensor means, thus forming image data describing the position of the catheter.

A further advantageous embodiment of the device in accordance with the invention includes imaging means for displaying the body region at the area of the guide wire, as well as for displaying the inserted guide wire itself and/or the inserted catheter. The imaging means may be capable of forming a two-dimensional image or also a three-dimensional image for display in a customary manner, for example, by means of a display screen.

The invention also relates to a computer program with program means for making a computer carry out the method in accordance with the invention when the program is executed on a computer.

Figure 2:
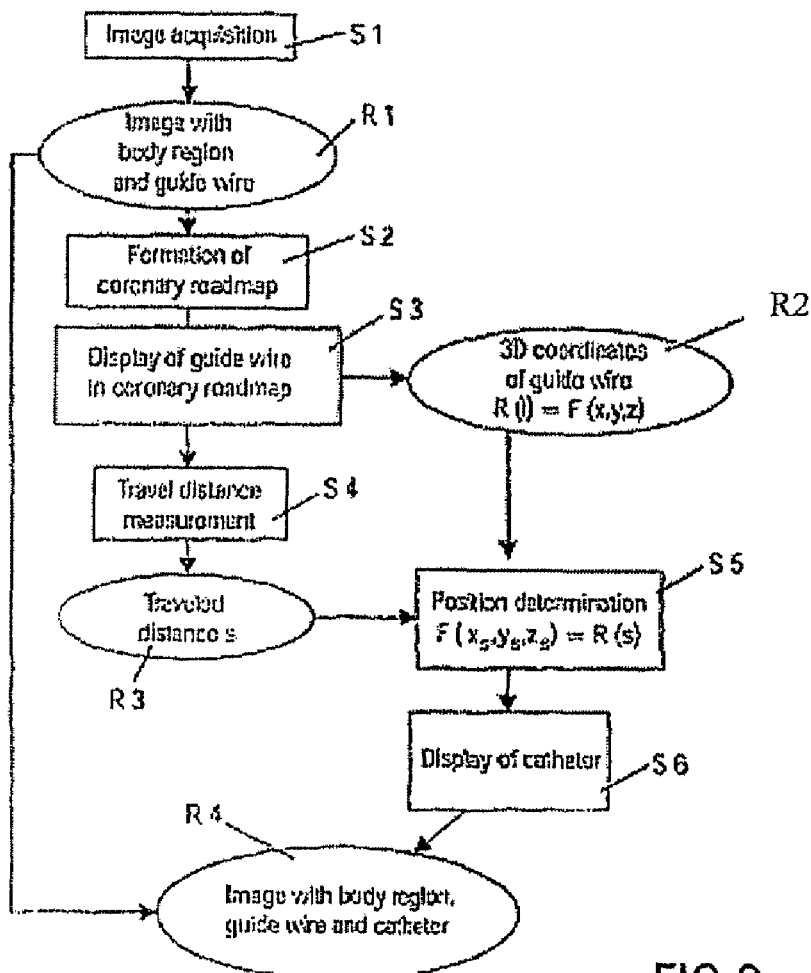
Figure 3:
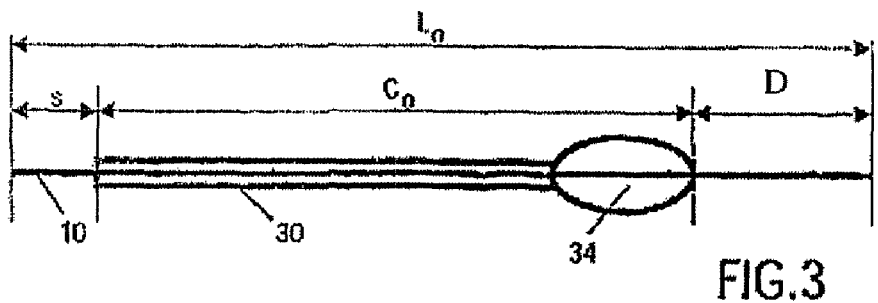

A preferred embodiment of the method and the device in accordance with the invention will be described in detail hereinafter with reference to the Figures. Therein:

FIG. 1 is a diagrammatic representation of an embodiment of the device in accordance with the invention with a guide wire introduced into a body, FIG. 2 shows a flow chart of a version of the method in accordance with the invention, and FIG. 3 is a diagrammatic representation of the lengths of the guide wire and a catheter arranged thereon.

In FIG. 1 a guide wire 10 has been introduced into a vascular system 21 of a body 20 via a body opening 22. The guide wire 10 has been slid into the vascular system 21 so far that from the opening 22 it extends beyond a constriction 23 in the vascular system 21. A catheter 30 has been threaded on the guide wire. The catheter 30 has been advanced through the vascular system 21, along the guide wire 10, so far that the end 33 of the catheter 30 within the vascular system 21 is situated just in front of the constriction 23. To the end 33 situated within the vascular system there is attached a dilatation bulb 34. The dilatation bulb 34 is merely an example and may be replaced by other known catheter-guided treatment devices.

The catheter 30 and the guide wire 10 pass through a feed device 40. The feed device includes feed wheels 41, 42. The feed wheels 41, 42 are situated at a distance from one another. The catheter 30 passes between the feed wheels 41, 42 and is frictionally engaged thereby.

Because of the frictional contact between the feed wheels 41, 42 and the catheter 30, the wheels 41, 42 rotate when the catheter 30 is manually advanced on the guide wire 10. Furthermore, the catheter 30 can be advanced on the guide wire 10 by driving the feed wheels 41, 42.

The feed wheels 41, 42 (or at least one of these feed wheels) are connected to sensor means (not shown) which measure the rotation of the feed wheels and hence measure the distance of travel of the catheter 30. The rotation sensor means are connected to a computer 50 and apply the measured distance to the computer.

FIG. 1 also shows an X-ray C-arm 60. This apparatus is of a known type as used for many medical imaging applications. The X-ray C-arm is arranged in such a manner that it is capable of imaging the body 20, that is, at least the body region in which the constriction 23 is situated. The X-ray C-arm 60 is also connected to the computer 50 and applies the image data to the computer.

The computer 50 calculates the position of the catheter 30, notably the position of the dilatation bulb 34 at the end 33 of the catheter 30, from the image data of the X-ray C-arm 60 and the distance of travel as presented by the rotation sensors of the feed device 40.

The computer 50 is connected to a monitor 70 which serves to display the body region around the constriction 23, the guide wire 10 at the area of this constriction and the catheter 30, that is, notably the end 33 thereof and the dilatation bulb 34 attached thereto.

Referring to FIG. 2, the method in accordance with the invention commences with an image acquisition step S1 in which an image R1 is acquired of the relevant body region and the guide wire.

In a next step S2 a coronary roadmap is formed from said image R1. Subsequently (S3), the guide wire is displayed in the coronary roadmap. As a result (R2) of this display, the coordinates $F(x,y,z)$ can be displayed separately in dependence on a parameter l. The parameter l denotes the distance between the guide wire segment to be displayed and the end of the guide wire.

During a next step S4 the distance traveled by the catheter on the guide wire is determined. This results in a traveled distance s (R3).

In order to determine the position in which the tip of the catheter is situated within the body, the traveled distance s can be used to determine the 3D co-ordinates of the tip of the catheter, the overall length of the guide wire and of the catheter 30 being known.

Referring to FIG. 3, the length $L_0$ of the guide wire and the length $C_0$ of the catheter being known, the distance D searched between the tip of the catheter and the front end of the guide wire can be simply determined in dependence on the traveled distance s by calculating D in conformity with the formula $$D = L_0 - C_0 - s.$$

Similarly, in particular when a two-dimensional imaging method is used, a marker may be provided on the guide wire, the distance between said marker and the extracorporal end of the guide wire being known. This marker is placed in relation to the lesion (for example, centrally with respect to the lesion, exactly behind the lesion or exactly in front of the lesion) by means of the imaging method. The catheter can then be exactly positioned by relating it to the extracorporal end of the guide wire.

Again referring to FIG. 2, after the determination of the position of the catheter or the tip of the catheter in dependence on the traveled distance s (S5), the catheter can be displayed (S6) and, using the previously acquired image with the body region and the guide wire R1, an image R4 can be formed which shows the body region, the guide wire and the catheter.

The invention claimed is:

1. A method of determining the position of a catheter comprising:

inserting a guide wire into a body in a body region of interest;

inserting the catheter into the body along the guide wire;
acquiring an image of the guide wire and the body region of interest;
measuring a distance traveled by the catheter on the guide wire;
determining a position of the guide wire in the body relative to the body region of interest based on the image; and
determining a position of the catheter in the body using the measured distance and the position of the guide wire in the body.

2. A method as claimed in claim 1, wherein an image is acquired of the body region, the position of the catheter being displayed in said image.

3. A method as claimed in claim 1, wherein the acquisition of the image of the body region and the guide wire is performed by means of two-dimensional or three-dimensional X-ray imaging.

4. A method as claimed in claim 3, wherein the body region and the guide wire are imaged by way of two essentially orthogonal projections and a three-dimensional image of the body region is formed from said projections by way of modeling.

5. A method as claimed in claim 1, wherein the acquisition of the images is performed by means of images of the body regions which have been shifted in time and triggered on the basis of the cardiac frequency.

6. A method as claimed in claim 1, wherein an image of the body region with the guide wire and the inserted catheter is acquired and displayed after the determination of the position of the catheter.

7. A method as claimed in claim 1, wherein the catheter is advanced by means of a drive device which measures the advancement of the catheter.

8. A method as claimed in claim 7, wherein an acoustic and/or optical signal is generated and/or an image acquisition is performed when the catheter reaches a target position.

9. A method of medical treatment comprising:
providing a guide wire having a marker thereon;
inserting a guide wire into a body in a body region of interest;
acquiring one or more images of the guide wire in the body region of interest;
adjusting the position of the guide wire using the one or more images until the marker is at a target point of the body region of interest;
inserting a catheter into the body along the guide wire;
acquiring another image of the guide wire and the body region of interest when the marker is at the target point;
measuring a distance traveled by the catheter on the guide wire; and
determining a position of an end of the catheter with respect to the target point using the measured distance and the position of the guide wire in the body from the another image.

10. The method of claim 9, further comprising:
providing a treatment device at the end of the catheter; and
providing treatment to the target point using the treatment device.

11. The method as claimed in claim 9, wherein at least one of the acquiring of one or more images and the acquiring of another image is through use of X-ray imaging.

12. The method as claimed in claim 9, further comprising presenting at least one of the one or more images and the another image on a display.

13. The method as claimed in claim 9, further comprising:
inserting the catheter into the body along the guide wire using a feeding device comprising a pair of drive wheels, wherein the catheter is positioned therebetween; and
measuring a distance traveled by the catheter on the guide wire using a sensor that measures the rotation of at least one of the pair of drive wheels.

* * * * *